United States Patent
Fournier et al.

(10) Patent No.: US 6,649,388 B2
(45) Date of Patent: Nov. 18, 2003

(54) POLYPEPTIDES DERIVED FROM JNK3

(75) Inventors: Alain Fournier, Chatenay Malabry (FR); Isabelle Maury, Virty sur Seine (FR); Qing Zhou-Liu, Chenneviers sur Marne (FR); Francine Desanlis-Cremond, Noisy le Grand (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/909,650

(22) Filed: Jul. 19, 2001

(65) Prior Publication Data
US 2002/0165386 A1 Nov. 7, 2002

Related U.S. Application Data

(63) Continuation of application No. PCT/FR00/00104, filed on Jan. 19, 2000.
(60) Provisional application No. 60/122,175, filed on Feb. 26, 1999.

(30) Foreign Application Priority Data

Jan. 20, 1999 (FR) .............................. 99 00586

(51) Int. Cl.$^7$ .......................... C12N 9/12; C12N 15/00; C12N 5/00; C12Q 1/68; C07H 21/04
(52) U.S. Cl. .................... 435/194; 435/320.1; 435/325; 435/252.3; 435/6; 536/23.2
(58) Field of Search ........................ 536/23.2; 435/194, 435/320.1, 252.3, 325, 6

(56) References Cited

U.S. PATENT DOCUMENTS

| | | | |
|---|---|---|---|
| 5,804,399 A | 9/1998 | Karin et al. | .................. 435/15 |
| 6,162,613 A | * 12/2000 | Su et al. | ........................ 435/15 |

FOREIGN PATENT DOCUMENTS

| | | |
|---|---|---|
| CA | 2148898 | 11/1995 |

OTHER PUBLICATIONS

Estus, et al, Altered Gene Expression in Neurons during Programmed Cell Death: Identification of c–jun as Necessary for Neuronal Apoptosis, Journal of Cell Biol., Vol 127, No. 6, Dec. 1994, pp. 1717–1727.

Galcheva–Gargova, et al, An Osmosensing Signal Transduction Pathway in Mammalian Cells, Science, vol. 265, Aug. 5, 1994, pp. 806–807.

Han, et al, A MAP Kinase Targeted by Endotoxin and Hyperosmolarity in Mammalian Cells, Science, vol. 265, Aug. 5, 1994, pp. 808–811.

Derijard, et al, JNK1: A Protein Kinase Stimulated by UV Light and Ha–Ras That Binds and Phosphorylates the c–Jun Activation Domain, Cell, Vol 76, Mar. 25, 1994, pp. 1025–1037.

Chung et al, One–step preparation of competent *Escherichia coli*: Transformation and storage of bacterial cells in the same solution, Proc. Natl. Acad. Sci, USA, vol. 86, Apr. 1989, pp. 2172–2175.

Wach et al, New Heterologous Modules For Classical or PCR–based Gene Disruptions in *Saccaromyces cerevisiae*, Yeast, vol. 10, (1994), pp. 1793–1808.

Gietz et al, Studies on the Transformation of Intact Yeast Cells by the LiAc/SS–DNA/PEG Procedure, Yeast, vol. 11, (1995), pp. 355–360.

Martin et al, Jun expression is found in neurons located in the vicinity of subacute plaques in patients with multiple sclerosis, Neurocience Letters 212, (1996) pp. 95–98.

Ham et al, A c–Jun Dominant Negative Mutant Protects Sympathetic Neurons against Programmed Cell Death, Neuron, vol. 14, May 1995, pp. 927–938.

Anderson et al, Increased Immunoreactivity for Jun– and FoS–Related Proteins in Alzheimer's Disease: Association with Pathology, Experimental Neurology 125, (1994), pp. 286–295.

Fields et al, The two–hybrid system: an assay for protein–protein interactions, TIG, vol. 10, No. 8, Aug. 1994, pp. 286–292.

Gupta et al, Selective interaction of JNK protein kinase isoforms with transcription factors, The EMBO Journal, vol. 15, No. 11, 1996, pp. 2760–2770.

Ito et al, JSAP1, a Novel Jun N–Terminal Protein Kinase (JNK)–Binding Protein That Functions as a Scaffold Factor in the JNK Signaling Pathway, Molecular And Cellular Biology, Novl. 1999, pp. 7539–7548.

Herdegen et al, The c–Jun transcription factor—bipotential mediator of neuronal death, survival and regeneration, TINS vol. 20, No. 5, 1997, pp. 227–231.

Herdegan et al, Lasting N–Terminal Phosphorylation of c–Jun and Activation of c–Jun N–Terminal Kinases after Neuronal Injury, The Journal of Neuroscience, Jul. 15, 1998, vol. 18(14), pp. 5124–5135.

Zhang et al, A splicing variant of a death domain protein that is regulated by a mitogen–activated kinase is a substrate for c–Jun N–terminal kinase in the human central nervous system, Proc. Natl. Acad. Sci, USA, vol. 95, Mar. 1998, pp. 2586–2591.

W. A. Marasco, Intrabodies: turning the humoral immune system outside in for intracellular immunization, Gene Therapy, vol. 4 (1997) pp. 11–15.

Yang et al, Absence of excitotoxity–induced apoptosis in the hippocampus of mice lacking the Jnk3 gene, Nature vol. 389, Oct. 1997, pp. 865–870.

(List continued on next page.)

*Primary Examiner*—Maryam Monshipouri
(74) *Attorney, Agent, or Firm*—William C. Coppola

(57) ABSTRACT

Provided herein are novel polypeptides that are derived from human JNK3 proteins, variants of such polypeptides, their corresponding nucleotide sequences, and their uses.

4 Claims, 5 Drawing Sheets

OTHER PUBLICATIONS

Sanger et al, DNA sequencing with chain–terminating inhibitors, Proc. Natl. Acad. Sci, USA, vol. 74, No. 12, Dec. 1997, pp. 5463–5467.

Wurgler–Murphy et al, Regulation of the *Saccharomyces cerevisiae* HOG1 Miogen–Activated Protein Kinase by the PTP2 and PTP3 Protein Tyrosine Phosphatases, Molecular And Cellular Biology, Mar., 1997, pp. 1289–1297.

Mohit et al, $p49^{3F12}$ Kinase: A Novel MAP Kinase Expressed in a Subset of Neurons in the Human Nervous System, Neuron, vol. 14, Jan. 1995, pp. 67–78.

* cited by examiner

| | | | | | | | | | | | | | | |
|---|---|---|---|---|---|---|---|---|---|---|---|---|---|---|
| hJNK3α1,3α2 | | | | | | | | | | | | | | |
| hJNK3α1,α2ΔN | ATG | AGC | CTC | CAT | TTC | TTA | TAC | TAC | TGC | AGT | GAA | CCA | ACA | TTG | GAT | AAA | ATT | GCC | TTT |
| hJNK3α139 | ATG | AGC | CTC | CAT | TTC | TTA | TAC | TAC | TGC | AGT | GAA | CCA | ACA | TTG | GAT | GTG | AAA | ATT | GCC | TTT |
| | ATG | AGC | CTC | CAT | TTC | TTA | TAC | TAC | TGC | AGT | GAA | CCA | ACA | TTG | GAT | GTG | AAA | ATT | GCC | TTT |

| hJNK3α1,3α2 | TGT | CAG | | | | | | | | GGA | TTC | GAT | AAA | CAA | GTG | GAT | GTG | TCA |
| hJNK3α1,α2ΔN | TGT | CAG | GTG | TGT | GTT | CCT | TAC | AGG | TAA | AAC | AAG | GGA | TTC | GAT | AAA | CAA | GTG | GAT | GTG | TCA |
| hJNK3α139 | TGT | CAG | | | | | | | | | | GGA | TTC | GAT | AAA | CAA | GTG | GAT | GTG | TCA |

| hJNK3α1,3α2 | TAT | ATT | GCC | AAA | CAT | TAC | AAC | ATG | AGC | AAA | AGT | GAC | AAC | CAG | TTC | TAC | AGT | GTG |
| hJNK3α1,α2ΔN | TAT | ATT | GCC | AAA | CAT | TAC | AAC | ATG | AGC | AAA | AGT | GAC | AAC | CAG | TTC | TAC | AGT | GTG |
| hJNK3α139 | TAT | ATT | GCC | AAA | CAT | TAC | AAC | ATG | AGC | AAA | AGT | GAC | AAC | CAG | TTC | TAC | AGT | GTG |

| hJNK3α1,3α2 | GAA | GTG | GGA | GAC | TCA | ACC | TTC | ACA | GTT | CTC | AAG | CGC | TAC | CAG | AAT | CTA | AAG | CCT | ATT | GGC |
| hJNK3α1,α2ΔN | GAA | GTG | GGA | GAC | TCA | ACC | TTC | ACA | GTT | CTC | AAG | GGC | TAC | CAG | AAT | CTA | AAG | CCT | ATT | GGC |
| hJNK3α139 | GAA | GTG | GGA | GAC | TCA | ACC | TTC | ACA | GTT | CTC | AAG | CGC | TAC | CAG | AAT | CTA | AAG | CCT | ATT | GGC |

FIGURE 1a

| | | | | | | | | | | | | | | |
|---|---|---|---|---|---|---|---|---|---|---|---|---|---|---|
| hJNK3α1,3α2 | TCT | GGG | GCT | CAG | GGC | ATA | GTT | TGT | GCC | GCG | TAT | GAT | GCT | GTC | CTT | GAC | AGA | AAT | GTG | GCC |
| hJNK3α1,α2ΔN | TCT | GGG | GCT | CAG | GGC | ATA | GTT | TGT | GCC | GCG | TAT | GAT | GCT | GTC | CTT | GAC | AGA | AAT | GTG | GCC |
| hJNK3α139 | TCT | GGG | GCT | CAG | GGC | ATA | GTT | TGT | GCC | GCG | TAT | GAT | GCT | GTC | CTT | GAC | AGA | AAT | GTG | GCC |
| hJNK3α1,3α2 | ATT | AAG | AAG | CTC | AGC | AGA | CCC | TTT | CAG | AAC | ACA | CAT | GCC | AAG | AGA | GCG | TAC | CGG | GAG |
| hJNK3α1,α2ΔN | ATT | AAG | AAG | CTC | AGC | AGA | CCC | TTT | CAG | AAC | ACA | CAT | GCC | AAG | AGA | GCG | TAC | CGG | GAG |
| hJNK3α139 | ATT | AAG | AAG | CTC | AGC | AGA | CCC | TTT | CAG | AAC | ACA | CAT | GCC | AAG | AGA | GCG | TAC | CGG | GAG |
| hJNK3α1,3α2 | CTG | GTC | CTC | ATG | AAG | TGT | GTG | AAC | CAT | AAA | AAC | ATT | ATT | AGT | TTA | AAT | GTC | TTC | ACA |
| hJNK3α1,α2ΔN | CTG | GTC | CTC | ATG | AAG | TGT | GTG | AAC | CAT | AAA | AAC | ATT | ATT | AGT | TTA | AAT | GTC | TTC | ACA |
| hJNK3α139 | CTG | GTC | CTC | ATG | AAG | TGT | GTG | AAC | CAT | AAA | AAC | ATT | ATT | AGT | TTA | AAT | GTC | TTC | ACA |
| hJNK3α1,3α2 | CCC | CAG | AAA | ACG | CTG | GAG | GAG | TTC | CAA | GAT | GTT | TAC | TTA | GTA | ATG | GAA | CTG | ATG | GAT | ... |
| hJNK3α1,α2ΔN | CCC | CAG | AAA | ACG | CTG | GAG | GAG | TTC | CAA | GAT | GTT | TAC | TTA | GTA | ATG | GAA | CTG | ATG | GAT | ... |
| hJNK3α139 | CCC | CAG | AAA | ACG | CTG | GAG | GAG | TTC | TAA | GAT | GTT | TAC | TTA | GTA | ATG | GAA | CTG | ATG | GAT | ... |

FIGURE 1b

```
hJNK3α1,α2ΔN   ATG AGC CTC CAT TTC TTA TAC TAC TGC AGT GAA CCA ACA TTG GAT GTG AAA ATT GCC TTT
rSAPKβ         ATG AGC CTC CAT TTC TTA TAC TAC TGC AGT GAA CCA ACC TTG GAT GTG AAA ATT GCC TTT
                                                                       * hJNK3α1,α2ΔN   TGT CAG GTG TGT GTT CCT TAC AGG TAA AAC AAG GGA TTC GAT AAA CAA GTG GAT GTG TCA
rSAPKβ         TGT CAG GTG TGT GTT CCT TAC AGG TAA AACAAAG GGA TTC GAC AAA CAC GTG GAT GTG TCT
                                                             *          *               * hJNK3α1,α2ΔN   TAT ATT GCC AAA CAT TAC AAC ATG AGC AAA AGC AAA GTT GAC AAC CAG TTC TAC AGT ...
rSAPKβ         TCT GTT GTC AAA CAT TAC AAC ATG AGC AAA AGC AAA GTA GAT AAC CAG TTC TAC AGT ...
                *   *   *                                        *   *
```

FIGURE 2

```
hJNK3α1     1   MSLHFLYYCS EPTLDVKIAF CQGFDKQVDV SYIAKHYNMS KSKVDNQFYS VEVGDSTFTV
hJNK3α2         MSLHFLYYCS EPTLDVKIAF CQGFDKQVDV SYIAKHYNMS KSKVDNQFYS VEVGDSTFTV
hJNK3α1Δ                                                MS KSKVDNQFYS VEVGDSTFTV
hJNK3α2Δ                                                MS KSKVDNQFYS VEVGDSTFTV
hJNK3α139       MSLHFLYYCS EPTLDVKIAF CQGFDKQVDV SYIAKHYNMS KSKVDNQFYS VEVGDSTFTV hJNK3α1    61   LKRYQNLKPI GSGAQGIVCA AYDAVLDRNV AIKKLSRPFQ NQTHAKRAYR ELVLMKCVNH
hJNK3α2         LKRYQNLKPI GSGAQGIVCA AYDAVLDRNV AIKKLSRPFQ NQTHAKRAYR ELVLMKCVNH
hJNK3α1Δ        LKRYQNLKPI GSGAQGIVCA AYDAVLDRNV AIKKLSRPFQ NQTHAKRAYR ELVLMKCVNH
hJNK3α2Δ        LKRYQNLKPI GSGAQGIVCA AYDAVLDRNV AIKKLSRPFQ NQTHAKRAYR ELVLMKCVNH
hJNK3α139       LKRYQNLKPI GSGAQGIVCA AYDAVLDRNV AIKKLSRPFQ NQTHAKRAYR ELVLMKCVNH hJNK3α1   121   KNIISLLNVF TPQKTLEEFQ DVYLVMELMD ANLCQVIQME LDHERMSYLL YQMLCGIKHL
hJNK3α2         KNIISLLNVF TPQKTLEEFQ DVYLVMELMD ANLCQVIQME LDHERMSYLL YQMLCGIKHL
hJNK3α1Δ        KNIISLLNVF TPQKTLEEFQ DVYLVMELMD ANLCQVIQME LDHERMSYLL YQMLCGIKHL
hJNK3α2Δ        KNIISLLNVF TPQKTLEEFQ DVYLVMELMD ANLCQVIQME LDHERMSYLL YQMLCGIKHL
hJNK3α139       KNIISLLNVF TPQKTLEEF
```

FIGURE 3a

```
hJNK3α1   181  HSAGIIHRDL KPSNIVVKSD CTLKILDFGL ARTAGTSFMM TPYVVTRYYR APEVILGMGY
hJNK3α2        HSAGIIHRDL KPSNIVVKSD CTLKILDFGL ARTAGTSFMM TPYVVTRYYR APEVILGMGY
hJNK3α1Δ       HSAGIIHRDL KPSNIVVKSD CTLKILDFGL ARTAGTSFMM TPYVVTRYYR APEVILGMGY
hJNK3α2Δ       HSAGIIHRDL KPSNIVVKSD CTLKILDFGL ARTAGTSFMM TPYVVTRYYR APEVILGMGY hJNK3α1   241  KENVDIWSVG CIMGEMVRHK ILFPGRDYID QWNKVIEQLG TPCPEFMKKL QPTVRNYVEN
hJNK3α2        KENVDIWSVG CIMGEMVRHK ILFPGRDYID QWNKVIEQLG TPCPEFMKKL QPTVRNYVEN
hJNK3α1Δ       KENVDIWSVG CIMGEMVRHK ILFPGRDYID QWNKVIEQLG TPCPEFMKKL QPTVRNYVEN
hJNK3α2Δ       KENVDIWSVG CIMGEMVRHK ILFPGRDYID QWNKVIEQLG TPCPEFMKKL QPTVRNYVEN hJNK3α1   301  RPKYAGLTFP KLFPDSLFPA DSEHNKLKAS QARDLLSKML VIDPAKRISV DDALQHPYIN
hJNK3α2        RPKYAGLTFP KLFPDSLFPA DSEHNKLKAS QARDLLSKML VIDPAKRISV DDALQHPYIN
hJNK3α1Δ       RPKYAGLTFP KLFPDSLFPA DSEHNKLKAS QARDLLSKML VIDPAKRISV DDALQHPYIN
hJNK3α2Δ       RPKYAGLTFP KLFPDSLFPA DSEHNKLKAS QARDLLSKML VIDPAKRISV DDALQHPYIN hJNK3α1   361  VWYDPAEVEA PPPQIYDKQL DEREHTIEEW KELIYKEVMN SEEKTKNGVV KGQPSPSAQV
hJNK3α2        VWYDPAEVEA PPPQIYDKQL DEREHTIEEW KELIYKEVMN SEEKTKNGVV KGQPSPSGAA
hJNK3α1Δ       VWYDPAEVEA PPPQIYDKQL DEREHTIEEW KELIYKEVMN SEEKTKNGVV KGQPSPSAQV
hJNK3α2Δ       VWYDPAEVEA PPPQIYDKQL DEREHTIEEW KELIYKEVMN SEEKTKNGVV KGQPSPSGAA hJNK3α1   421  QQ
hJNK3α2        VNSSESLPP- SSSVNDISSMS TDQTLASDTD SSLEASAGPL GCCR
hJNK3α1Δ       QQ
hJNK3α2Δ  421  VNSSESLPP- SSSVNDISSMS TDQTLASDTD SSLEASAGPL GCCR
```

FIGURE 3b

SEQUENCE LISTING

```
<160> NUMBER OF SEQ ID NOS: 29

<210> SEQ ID NO 1
<211> LENGTH: 48
<212> TYPE: DNA
<213> ORGANISM: homo sapiens

<400> SEQUENCE: 1
gcgggatcct atgagcctcc atttcttata ctactgcagt gaaccaac         48

<210> SEQ ID NO 2
<211> LENGTH: 40
<212> TYPE: DNA
<213> ORGANISM: homo sapiens

<400> SEQUENCE: 2
cacggtacct cactgctgca cctgtgctga aggagaaggc                  40

<210> SEQ ID NO 3
```

-continued

```
<211> LENGTH: 38
<212> TYPE: DNA
<213> ORGANISM: homo sapiens

<400> SEQUENCE: 3
ggcggtacct cacctgcaac aacccagggg tcctgccg                            38

<210> SEQ ID NO 4
<211> LENGTH: 40
<212> TYPE: DNA
<213> ORGANISM: homo sapiens

<400> SEQUENCE: 4
tcccccggga tccaaaatga gcctccattt cttatactac                          40

<210> SEQ ID NO 5
<211> LENGTH: 36
<212> TYPE: DNA
<213> ORGANISM: homo sapiens

<400> SEQUENCE: 5
tcccccgggc tcgagtcact gctgcacctg tgctga                              36

<210> SEQ ID NO 6
<211> LENGTH: 36
<212> TYPE: DNA
<213> ORGANISM: homo sapiens

<400> SEQUENCE: 6
tcccccgggc tcgagtcacc tgcaacaacc cagggg                              36

<210> SEQ ID NO 7
<211> LENGTH: 39
<212> TYPE: DNA
<213> ORGANISM: homo sapiens

<400> SEQUENCE: 7
tcccccggga tccaaaatga gcaaaagcaa agttgacaa                           39

<210> SEQ ID NO 8
<211> LENGTH: 36
<212> TYPE: DNA
<213> ORGANISM: homo sapiens

<400> SEQUENCE: 8
tcccccgggc tcgagtcact gctgcacctg tgctga                              36

<210> SEQ ID NO 9
<211> LENGTH: 36
<212> TYPE: DNA
<213> ORGANISM: homo sapiens

<400> SEQUENCE: 9
tcccccgggc tcgagtcacc tgcaacaacc cagggg                              36

<210> SEQ ID NO 10
<211> LENGTH: 37
<212> TYPE: DNA
<213> ORGANISM: homo sapiens

<400> SEQUENCE: 10
tcccccggga tccaaaatga gcagaagcaa gcgtgac                             37
```

```
<210> SEQ ID NO 11
<211> LENGTH: 33
<212> TYPE: DNA
<213> ORGANISM: homo sapiens

<400> SEQUENCE: 11
tcccccgggc tcgagtcact gctgcacctg tgc                                    33

<210> SEQ ID NO 12
<211> LENGTH: 37
<212> TYPE: DNA
<213> ORGANISM: homo sapiens

<400> SEQUENCE: 12
tcccccggga tccaaaatga gcgacagtaa atgtgac                                37

<210> SEQ ID NO 13
<211> LENGTH: 36
<212> TYPE: DNA
<213> ORGANISM: homo sapiens

<400> SEQUENCE: 13
tcccccgggc tcgagttact gctgcatctg tgctga                                 36

<210> SEQ ID NO 14
<211> LENGTH: 39
<212> TYPE: DNA
<213> ORGANISM: homo sapiens

<400> SEQUENCE: 14
taggacacag atattcggta cagctgaagc ttcgtacgc                              39

<210> SEQ ID NO 15
<211> LENGTH: 42
<212> TYPE: DNA
<213> ORGANISM: homo sapiens

<400> SEQUENCE: 15
gacctttgtt tccaccagct gcataggcca ctagtggatc tg                          42

<210> SEQ ID NO 16
<211> LENGTH: 40
<212> TYPE: DNA
<213> ORGANISM: homo sapiens

<400> SEQUENCE: 16
accactaacg aggaattcat taggacacag atattcggta                             40

<210> SEQ ID NO 17
<211> LENGTH: 40
<212> TYPE: DNA
<213> ORGANISM: homo sapiens

<400> SEQUENCE: 17
tttgcagcta catgatcgct gacctttgtt tccaccagct                             40

<210> SEQ ID NO 18
<211> LENGTH: 20
<212> TYPE: DNA
<213> ORGANISM: homo sapiens

<400> SEQUENCE: 18
gagtagtaat tactttcttg                                                   20
```

<210> SEQ ID NO 19
<211> LENGTH: 23
<212> TYPE: DNA
<213> ORGANISM: homo sapiens

<400> SEQUENCE: 19
ccgtgacaaa atatatatct tcc                                           23

<210> SEQ ID NO 20
<211> LENGTH: 20
<212> TYPE: DNA
<213> ORGANISM: homo sapiens

<400> SEQUENCE: 20
gagtagtaat tactttcttg                                               20

<210> SEQ ID NO 21
<211> LENGTH: 19
<212> TYPE: DNA
<213> ORGANISM: homo sapiens

<400> SEQUENCE: 21
ggatcttgcc atcctatgg                                                19

<210> SEQ ID NO 22
<211> LENGTH: 1306
<212> TYPE: DNA
<213> ORGANISM: homo sapiens

<400> SEQUENCE: 22
atgagcctcc atttcttata ctactgcagt gaaccaacat tggatgtgaa aattgccttt     60
tgtcaggtgt gtgttcctta caggtaaaac aagggattcg ataaacaagt ggatgtgtca   120
tatattgcca acattacaa catgagcaaa agcaaagttg acaaccagtt ctacagtgtg    180
gaagtgggag actcaacctt cacagttctc aagcgctacc agaatctaaa gcctattggc   240
tctgggctc agggcatagt ttgtgccgcg tatgatgctg tccttgacag aaatgtggcc    300
attaagaagc tcagcagacc ctttcagaac caaacacatg ccaagagagc gtaccgggag   360
ctggtcctca tgaagtgtgt gaaccataaa acattatta gtttattaaa tgtcttcaca    420
ccccagaaaa cgctggagga gttccaagat gtttacttag taatggaact gatggatgcc   480
aacttatgtc aagtgattca gatggaatta gaccatgagc aatgtctta cctgctgtac    540
caaatgttgt gtggcattaa gcacctccat tctgctggaa ttattcacag ggatttaaaa    600
ccaagtaaca ttgtagtcaa gtctgattgc acattgaaaa tcctggactt tggactggcc    660
aggacagcag gcacaagctt catgatgact ccatatgtgg tgacacgtta ttacagagcc   720
cctgaggtca tcctggggat gggctacaag gagaacgtgg atatatggtc tgtgggatgc    780
attatgggag aaatggttcg ccacaaaatc ctctttccag aagggactaa tattgaccag    840
tggaataagg taattgaaca actaggaaca ccatgtccag aattcatgaa gaaattgcaa    900
cccacagtaa gaaactatgt ggagaatcgg cccagtatg cgggactcac cttccccaaa    960
ctcttcccag attccctctt cccagcggac tccgagcaca taaaactcaa gccagccaa   1020
gccagggact tgttgtcaaa gatgctagtg attgacccag caaaaagaat atcagtggac   1080
gacgccttac agcatcccta catcaacgtc tggtatgacc cagccgaagt ggaggcgcct   1140
ccacctcaga tatatgacaa gcagttggat gaaagagaac acacaattga agaatggaaa   1200
gaacttatct acaaggaagt aatgaattca gaagaaaaga ctaaaaatgg tgtagtaaaa   1260

```
ggacagcctt ctccttcagc acaggtgcag cagtgaacag cagtga                   1306

<210> SEQ ID NO 23
<211> LENGTH: 1422
<212> TYPE: DNA
<213> ORGANISM: homo sapiens

<400> SEQUENCE: 23
atgagcctcc atttcttata ctactgcagt gaaccaacat tggatgtgaa aattgccttt      60
tgtcaggtgt gtgttcctta caggtaaaac aagggattcg ataaacaagt ggatgtgtca     120
tatattgcca acattacaa catgagcaaa agcaaagttg acaaccagtt ctacagtgtg      180
gaagtgggag actcaacctt cacagttctc aagcgctacc agaatctaaa gcctattggc     240 tctgggctc agggcatagt ttgtgccgcg tatgatgctg tccttgacag aaatgtggcc      300
attaagaagc tcagcagacc ctttcagaac caaacacatg ccaagagagc gtaccgggag     360
ctggtcctca tgaagtgtgt gaaccataaa acattatta gtttattaaa tgtcttcaca      420
ccccagaaaa cgctggagga gttccaagat gtttacttag taatggaact gatggatgcc     480
aacttatgtc aagtgattca gatggaatta gaccatgagc aatgtctta cctgctgtac      540 caaatgttgt gtggcattaa gcacctccat tctgctggaa ttattcacag ggatttaaaa     600
ccaagtaaca ttgtagtcaa gtctgattgc acattgaaaa tcctggactt tggactggcc     660
aggacagcag gcacaagctt catgatgact ccatatgtgg tgacacgtta ttacagagcc     720
cctgaggtca tcctggggat gggctacaag gagaacgtgg atatatggtc tgtgggatgc     780
attatgggag aaatggttcg ccacaaaatc ctctttccag aagggactg tattgaccag     840 tggaataagg taattgaaca actaggaaca ccatgtccag aattcatgaa gaaattgcaa     900
cccacagtaa gaaactatgt ggagaatcgg cccaagtatg cgggactcac cttccccaaa     960
ctcttcccag attccctctt cccagcggac tccgagcaca taaaactcaa agccagccaa    1020
gccagggact tgttgtcaaa gatgctagtg attgacccag caaaaagaat atcagtggac    1080
gacgccttac agcatcccta catcaacgtc tggtatgacc cagccgaagt ggaggcgcct    1140
ccacctcaga tatatgacaa gcagttggat gaaagagaac acacaattga agaatggaaa    1200
gaacttatct acaaggaagt aatgaattca gaagaaaaga ctaaaaatgg tgtagtaaaa    1260
ggacagcctt ctccttcagg tgcagcagtg aacagcagtg agagtctccc tccatcctcg    1320
tctgtcaatg acatctcctc catgtccacc gaccagaccc tggcatctga cactgacagc    1380
agcctggaag cctcggcagg accctgggt tgttgcaggt ga                        1422

<210> SEQ ID NO 24
<211> LENGTH: 426
<212> TYPE: PRT
<213> ORGANISM: homo sapiens

<400> SEQUENCE: 24

Met Ser Lys Ser Lys Val Asp Asn Gln Phe Tyr Ser Val Glu Val Gly
1               5                   10                  15

Asp Ser Thr Phe Thr Val Leu Lys Arg Tyr Gln Asn Leu Lys Pro Ile
                20                  25                  30

Gly Ser Gly Ala Gln Gly Ile Val Cys Ala Ala Tyr Asp Ala Val Leu
            35                  40                  45

Asp Arg Asn Val Ala Ile Lys Lys Leu Ser Arg Pro Phe Gln Asn Gln
        50                  55                  60
```

| | | | | | | | | | | | | |
|---|---|---|---|---|---|---|---|---|---|---|---|---|
|Thr|His|Ala|Lys|Arg|Ala|Tyr|Arg|Glu|Leu|Val|Leu|Met|Lys|Cys|Val|
|65| | | |70| | | |75| | | |80|

Asn His Lys Asn Ile Ile Ser Leu Leu Asn Val Phe Thr Pro Gln Lys
 85 90 95

Thr Leu Glu Glu Phe Gln Asp Val Tyr Leu Val Met Glu Leu Met Asp
 100 105 110

Ala Asn Leu Cys Gln Val Ile Gln Met Glu Leu Asp His Glu Arg Met
 115 120 125

Ser Tyr Leu Leu Tyr Gln Met Leu Cys Gly Ile Lys His Leu His Ser
 130 135 140

Ala Gly Ile Ile His Arg Asp Leu Lys Pro Ser Asn Ile Val Val Lys
145 150 155 160

Ser Asp Cys Thr Leu Lys Ile Leu Asp Phe Gly Leu Ala Arg Thr Ala
 165 170 175

Gly Thr Ser Phe Met Met Thr Pro Tyr Val Val Thr Arg Tyr Tyr Arg
 180 185 190

Ala Pro Glu Val Ile Leu Gly Met Gly Tyr Lys Glu Asn Val Asp Ile
 195 200 205

Trp Ser Val Gly Cys Ile Met Gly Glu Met Val Arg His Lys Ile Leu
 210 215 220

Phe Pro Gly Arg Asp Tyr Ile Asp Gln Trp Asn Lys Val Ile Glu Gln
225 230 235 240

Leu Gly Thr Pro Cys Pro Glu Phe Met Lys Lys Leu Gln Pro Thr Val
 245 250 255

Arg Asn Tyr Val Glu Asn Arg Pro Lys Tyr Ala Gly Leu Thr Phe Pro
 260 265 270

Lys Leu Phe Pro Asp Ser Leu Phe Pro Ala Asp Ser Glu His Asn Lys
 275 280 285

Leu Lys Ala Ser Gln Ala Arg Asp Leu Leu Ser Lys Met Leu Val Ile
 290 295 300

Asp Pro Ala Lys Arg Ile Ser Val Asp Asp Ala Leu Gln His Pro Tyr
305 310 315 320

Ile Asn Val Trp Tyr Asp Pro Ala Glu Val Glu Ala Pro Pro Pro Gln
 325 330 335

Ile Tyr Asp Lys Gln Leu Asp Glu Arg Glu His Thr Ile Glu Glu Trp
 340 345 350

Lys Glu Leu Ile Tyr Lys Glu Val Met Asn Ser Glu Glu Lys Thr Lys
 355 360 365

Asn Gly Val Val Lys Gly Gln Pro Ser Pro Ser Gly Ala Ala Val Asn
 370 375 380

Ser Ser Glu Ser Leu Pro Pro Ser Ser Ser Val Asn Asp Ile Ser Ser
385 390 395 400

Met Ser Thr Asp Gln Thr Leu Ala Ser Asp Thr Asp Ser Ser Leu Glu
 405 410 415

Ala Ser Ala Gly Pro Leu Gly Cys Cys Arg
 420 425

<210> SEQ ID NO 25
<211> LENGTH: 420
<212> TYPE: DNA
<213> ORGANISM: homo sapiens

<400> SEQUENCE: 25
atgagcctcc atttcttata ctactgcagt gaaccaacat tggatgtgaa aattgccttt    60

```
tgtcagggat tcgataaaca agtggatgtg tcatatattg ccaaacatta caacatgagc    120
aaaagcaaag ttgacaacca gttctacagt gtggaagtgg gagactcaac cttcacagtt    180
ctcaagcgct accagaatct aaagcctatt ggctctgggg ctcagggcat agtttgtgcc    240
gcgtatgatg ctgtccttga cagaaatgtg gccattaaga agctcagcag acccttcag     300 aaccaaacac atgccaagag agcgtaccgg gagctggtcc tcatgaagtg tgtgaaccat    360
aaaaacatta ttagtttatt aaatgtcttc acaccccaga aaacgctgga ggagttctaa    420
```

<210> SEQ ID NO 26
<211> LENGTH: 139
<212> TYPE: PRT
<213> ORGANISM: homosapiens
<400> SEQUENCE: 26

Met Ser Leu His Phe Leu Tyr Tyr Cys Ser Glu Pro Thr Leu Asp Val
1               5                   10                  15

Lys Ile Ala Phe Cys Gln Gly Phe Asp Lys Gln Val Asp Val Ser Tyr
            20                  25                  30

Ile Ala Lys His Tyr Asn Met Ser Lys Ser Lys Val Asp Asn Gln Phe
        35                  40                  45

Tyr Ser Val Glu Val Gly Asp Ser Thr Phe Thr Val Leu Lys Arg Tyr
    50                  55                  60

Gln Asn Leu Lys Pro Ile Gly Ser Gly Ala Gln Gly Ile Val Cys Ala
65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe
    130                 135

<210> SEQ ID NO 27
<211> LENGTH: 114
<212> TYPE: DNA
<213> ORGANISM: homo sapiens
<400> SEQUENCE: 27

```
atgagcctcc atttcttata ctactgcagt gaaccaacat tggatgtgaa aattgccttt    60
tgtcagggat tcgataaaca agtggatgtg tcatatattg ccaaacatta caac          114
```

<210> SEQ ID NO 28
<211> LENGTH: 38
<212> TYPE: PRT
<213> ORGANISM: homo sapiens
<400> SEQUENCE: 28

Met Ser Leu His Phe Leu Tyr Tyr Cys Ser Glu Pro Thr Leu Asp Val
1               5                   10                  15

Lys Ile Ala Phe Cys Gln Gly Phe Asp Lys Gln Val Asp Val Ser Tyr
            20                  25                  30

Ile Ala Lys His Tyr Asn
        35

<210> SEQ ID NO 29
<211> LENGTH: 176

-continued

```
<212> TYPE: PRT
<213> ORGANISM: homo sapiens

<400> SEQUENCE: 29

Trp Ser Val Gly Cys Ile Met Gly Glu Met Val Arg His Lys Ile Leu
1               5                   10                  15

Phe Pro Gly Arg Asp Tyr Ile Asp Gln Trp Asn Lys Val Ile Glu Gln
            20                  25                  30

Leu Gly Thr Pro Cys Pro Glu Phe Met Lys Lys Leu Gln Pro Thr Val
        35                  40                  45

Arg Asn Tyr Val Glu Asn Arg Pro Lys Tyr Ala Gly Leu Thr Phe Pro
    50                  55                  60

Lys Leu Phe Pro Asp Ser Leu Phe Pro Ala Asp Ser Glu His Asn Lys
65                  70                  75                  80

Leu Lys Ala Ser Gln Ala Arg Asp Leu Leu Ser Lys Met Leu Val Ile
                85                  90                  95

Asp Pro Ala Lys Arg Ile Ser Val Asp Asp Ala Leu Gln His Pro Tyr
            100                 105                 110

Ile Asn Val Trp Tyr Asp Pro Ala Glu Val Glu Ala Pro Pro Pro Gln
            115                 120                 125

Ile Tyr Asp Lys Gln Leu Asp Glu Arg Glu His Thr Ile Glu Glu Trp
            130                 135                 140

Lys Glu Leu Ile Tyr Lys Glu Val Met Asn Ser Glu Glu Lys Thr Lys
145                 150                 155                 160

Asn Gly Val Val Lys Gly Gln Pro Ser Pro Ser Ala Gln Val Gln Gln
                165                 170                 175
```

POLYPEPTIDES DERIVED FROM JNK3

CROSS REFERENCE TO RELATED APPLICATIONS

This application is a continuation application of PCT/FR00/00104, having an international filing date of Jan. 19, 2000, and which claims priority from FR 99 00586 filed Jan. 20, 1999 and U.S. 60/122,175, filed Feb. 26, 1999, wherein said applications are hereby incorporated by reference herein in their entireties.

The present invention relates to the field of biology and of the regulation of the signal transduction pathways which respond to extracellular stimuli. More specifically, the present invention is concerned with novel polypeptides which are derived from the human JNK3 protein, their variants, the corresponding nucleotide sequences, and their uses.

The protein JNK (c-jun N-terminal kinase), also termed SAPK (stress-activated protein kinase), belongs to the family of MAP (mitogen-activated protein) kinases. It is involved in the signal transduction pathways which respond to extracellular stimuli (for example, proinflammatory cytokines or environmental stresses). Its activation requires the phosphorylation of threonine 221 and tyrosine 223 within a highly conserved T-P-Y tripeptide motif located in the kinase domain (Dérijard et al. 1994). The substrates of JNK are transcription factors such as c-jun (phosphorylated on serine 63 and serine 73), ATF-2 (phosphorylated on threonine 69 and threonine 71) and Elk-1.

The JNK proteins exhibit a large number of isoforms, and ten isoforms have been recorded to date. They derive from three different genes, termed JNK1, JNK2 and JNK3. The JNK1 and JNK2 genes encode two isoforms, α and β, by means of alternative splicing (Gupta et al. 1996). For each isoform, α and β, there exists a short version and a version which is elongated C-terminally. The short version is linked to the insertion, during the alternative splicing, of five nucleotides which supply a termination codon.

The proteins JNK3α1 and JNK3α2 are the only two isoforms of JNK3 which have so far been recorded. They differ from JNK1 or JNK2 by, inter alia, an N-terminal extension of 38 amino acids whose function has not yet been established. The rat JNK3 homologue, termed SAPKβ, does not exhibit this distinctive feature.

The tissue distribution of the isoforms is very diverse, with variable levels of expression. However, it has been demonstrated that, while the JNK3 isoforms are more selectively expressed in the brain (for example in the hippocampus or in the cerebellum (Mohit et al. 1995)), they are also expressed in the heart and the testes.

While a growing number of results underline the importance of JNK3 in the phenomena of neurodegeneration and neuronal death by apoptosis, the mode of action of JNK3 remains unknown.

It has been shown that the neurones of the CA1 region of the hippocampus of patients who have suffered a period of hypoxia exhibit strong JNK3 immunoreactivity within the nuclei whereas JNK3 immunoreactivity is diffuse and exclusively cytoplasmic in control samples (Zhang et al. 1998). Furthermore, deletion of the JNK3 gene in mice results in resistance to kainic acid, which is an agonist of the glutamate receptors involved in the phenomena of excitotoxicity. The authors (Yang et al. 1997) provide a detailed description of the reduction in the epileptic effects and the prevention of the neuronal death by apoptosis in the hippocampus following injection of kainic acid into these mice which have been deleted for JNK3. Lastly, one of the preferred substrates of JNK3 is the transcription factor c-Jun, which is one of the components of the AP1 complex, which is itself heavily involved in functions of survival and neuronal degeneration. The c-Jun factor appears to have a double function i.e. both in cell death and in neuronal protection (Herdegen et al. 1997). Suppression of the expression of c-Jun or inhibition of its function protects the hippocampal and sympathetic neurones from cell death in culture (Estus et al. 1994, Ham et al. 1995). Finally, while expression of c-Jun is increased in apoptotic neurones which are degenerating following ischaemia, nerve section or irradiation, it is also increased in biopsies taken from patients afflicted with neurodegenerative pathologies such as multiple sclerosis, amyotrophic lateral sclerosis and Alzheimer's disease, Parkinson's disease and Huntington's disease (Anderson et al. 1994, Herdegen et al. 1998, Martin et al. 1996).

While the JNK3 protein kinase nowadays appears to be one of the key elements involved in neuronal degeneration, the precise nature of its mode of action is unknown. In this regard, the identification of new natural isoforms of JNK3 represents a major challenge for understanding the mechanism of action of this protein in the phenomena of neuronal degeneration and for identifying novel targets for aiming at therapeutically.

The present invention describes the detection, cloning and characterization of novel polypeptides derived from JNK3.

The present invention results from characterizing three novel isoforms of human JNK3 termed hJNK3α139, JNK3ΔNα1 and JNK3ΔNα2. It ensues, more particularly, from the demonstration that two of these isoforms, i.e. JNK3ΔNα1 and JNK3ΔNα2, lack the N-terminal extension which characterizes the known isoforms of JNK3 and the demonstration that these isoforms JNK3ΔNα1 and JNK3ΔNα2 exhibit properties which are different from those of the previously described isoforms of JNK3. It furthermore ensues from the discovery that these novel isoforms which lack the N-terminal extension unexpectedly share properties in common with the JNK1β1 and JNK2α1 isoforms.

The identification of these novel isoforms of JNK3 makes it possible to envisage a large number of applications. These applications cover, in particular, identifying novel neuroprotective compounds which are able to interact specifically with these isoforms. These compounds can be used for preventing and treating different pathologies which are brought about by neuronal degeneration, among which may be mentioned Alzheimer's disease, Huntington's disease and Parkinson's disease, senile dementia and dementia due to AIDS, cranial traumas, cerebral oedemas, hypoxias and anoxias. These novel isoforms can also be used in molecular modelling for achieving an improved understanding of the structure and function of these enzymes and their involvement in pathologies which implicate one or more isoforms of JNK3. Finally, these isoforms of JNK3 are also useful for detecting novel proteins which are involved in intracellular signalling pathways which are specific to each of them. It is thus possible to identify novel relevant targets which are involved in degenerative neuropathologies.

The invention firstly relates to polypeptides which are derived from the JNK3α1 or JNK3α2 isoforms and which contain an N-terminal or C-terminal deletion. According to a first embodiment, the derivatives are derivatives which contain an N-terminal deletion corresponding to the first 38 amino acids of these isoforms. According to another variant, the derivatives are derivatives which contain a deletion of the C-terminal amino acids from amino acid 139 onwards.

Preferably, the derivatives according to the invention are polypeptides which are selected from the sequences SEQ ID No. 23, SEQ ID No. 25 and SEQ ID No. 27, or a variant of these sequences.

Within the meaning of the invention, the term variant refers to any polypeptide whose structure differs from a polypeptide selected from the sequences SEQ ID No. 23 or SEQ ID No. 25 or SEQ ID No. 27 by one or more modifications of a genetic, biochemical and/or chemical nature and which preserves at least one of the biological properties of said polypeptide. The modification can, in particular, be any mutation, substitution, deletion, addition and/or modification of one or more residues. Such derivatives can be generated for different purposes, such as, in particular, that of improving their level of production, that of increasing their resistance to proteases or of improving their passage across cell membranes, that of increasing their therapeutic efficacy or of reducing their side effects, that of increasing the affinity of the polypeptides for their sites of interaction, or that of conferring novel pharmacokinetic and/or biological properties on it. Advantageously, the variants comprise deletions or mutations affecting amino acids whose presence does not play a decisive role in the activity of the derivative. Such amino acids can be identified, for example, by means of cell activity tests as described in the examples.

The invention also relates to a polypeptide as defined in accordance with the sequence SEQ ID No. 29 and which corresponds to the 1–38 fragment of the of the JNK3α1 or JNK3α2 forms.

The present invention furthermore relates to any nucleic acid which encodes a polypeptide derived from JNK3, as defined above.

The nucleic acid according to the invention can be a ribonucleic acid (RNA) or a deoxyribonucleic acid (DNA). Furthermore, it can be a genomic DNA (gDNA) or a complementary DNA (cDNA). The nucleic acid can be of human, animal, viral, synthetic or semisynthetic origin. It can be obtained in different ways, in particular by chemical synthesis using the sequences presented in the application and, for example, a nucleic acid synthesizer. The nucleic acid can also be obtained by screening libraries with specific probes, in particular those described in the application. It can also be obtained by means of mixed techniques including the chemical modification (elongation, deletion, substitution, etc.) of screened sequences obtained from libraries. Generally speaking, the nucleic acids of the invention can be prepared using any technique known to the skilled person.

Preferably, the nucleic acid according to the invention is a cDNA or an RNA. The nucleic acid according to the invention is advantageously selected from:

(a) all or part of the sequence SEQ ID No. 22 or SEQ ID No. 24 or SEQ ID No. 26, or their complementary strand, (b) any sequence which hybridizes with the (a) sequences and which encodes a derivative according to the invention, (c) the variants of (a) and (b) which result from the degeneracy of the genetic code.

The nucleic acid sequences according to the invention can also be used to create antisense oligonucleotides which can be used for regulating the expression of the different JNK3 isoforms. In this respect, the invention also relates to the antisense sequences whose expression in a target cell enables translation of cell mRNAs encoding JNK3ΔNα1 or JNK3ΔNα2 or hJNK3Nα139 or else JNK3α1 or JNK3α2 to be regulated specifically, by hybridizing antisense oligonucleotides with the sequences which are specific to the corresponding mRNAs. Such sequences can, for example, be transcribed, in the target cell, into RNAs which are complementary to the cell mRNAs of the different isoforms of JNK3 and thereby block their translation into protein, in accordance with the technique described in patent EP 140 308. Such sequences can consist of all or part of the nucleotide sequences SEQ ID No. 22, 24 or 26 as transcribed in the reverse orientation.

The invention also makes it possible to produce synthetic or non-synthetic nucleotide probes which are able to hybridize with the above-defined nucleotide sequences. Such probes can be used in vitro as a diagnostic tool for detecting the expression or overexpression of the different JNK3 isoforms or else for detecting genetic anomalies (poor splicing, polymorphism, point mutations, etc.). These probes can also be used for detecting and isolating homologous nucleic acid sequences, which encode peptides as previously defined, from other cell sources, preferably cells of human origin. While the probes of the invention generally comprise at least 17 bases and advantageously at least 300 bases, they can also comprise up to the entirety of one of the above-mentioned sequences or their complementary strand. Preferably, these probes are labelled prior to being used. Various techniques known to the skilled person can be employed for this purpose (radioactive, enzymic, etc. labelling).

The nucleotide probes can be employed, in particular by means of PCR, as a diagnostic tool for identifying:

either the isoforms which encode JNK3ΔNα1 or α2, using an oligonucleotide which corresponds to the insertion sequence of 27 nucleotides which is specific to SEQ ID No. 22 and 24 and which is located 5' of the initiation codon, and an oligonucleotide which is common to all the JNK3 isoforms;

or the isoforms which encode the JNK3s which have been previously described in the literature, using an oligonucleotide which corresponds to the sequence which is located on either side of the insertion region which is present in the sequence of JNK3ΔNα1 or α2, and an oligonucleotide which is common to all the JNK3 isoforms.

The diagnosis can also be effected by means of Northern blotting (Maniatis, T. et al. 1989) in order to identify:

either the isoforms which encode JNK3ΔNα1 or α2, using an oligonucleotide probe which corresponds to the insertion sequence of 27 nucleotides which is specific for SEQ ID No. 22 and 24 and which is located 5' of the initiation codon;

or the isoforms which encode the JNK3s which have been previously described in the literature, using an oligonucleotide probe which corresponds to the sequence of JNK3 which is located on either side of the insertion region which is present in the sequence of JNK3ΔNα1 or α2.

The present invention also relates to any expression cassette which comprises a nucleic acid as defined above, a promoter which enables it to be expressed and a transcription termination signal.

The invention furthermore relates to any vector which comprises a nucleotide sequence according to the invention or an expression cassette such as defined above. The vector of the invention can, for example, be a plasmid, a cosmid or any DNA which is not encapsidated by a virus, a phage, an artificial chromosome, a recombinant virus, etc. The vector is preferably a plasmid or a recombinant virus.

Those viral vectors in accordance with the invention which may, in particular, be mentioned are the vectors of the adenovirus, retrovirus, adeno-associated virus (AAV), herpes virus or vaccinia virus type. The present application also relates to defective recombinant viruses which comprise a heterologous nucleic acid sequence which encodes a polypeptide according to the invention. Such vectors can be used in gene therapy for treating peripheral traumas such as, in particular, traumas of the spinal cord or retinal degeneration.

The present invention also relates to host cells which are transformed with a nucleic acid which includes a nucleotide sequence or a vector according to the invention. The cell hosts which can be used for producing the polypeptides according to the invention can equally well be eukaryotic hosts or prokaryotic hosts. Suitable eukaryotic hosts which may be mentioned are animal cells, yeasts or fungi. Yeasts which may in particular be mentioned are yeasts of the genus Saccharomyces, Kluyveromyces, Pichia, Schwanniomyces, or Hansenula. Animal cells which may be mentioned are Sf9 insect cells, COS, CHO or C127 cells, human neuroblastoma cells, etc. Fungi which may more particularly be mentioned are Aspergillus ssp. or Trichoderma ssp. The prokaryotic hosts which are preferably employed are the following bacteria E. coli, Bacillus or Streptomyces.

According to a preferred embodiment, the host cells are advantageously represented by strains of recombinant yeasts. Preferably, the host cells comprise at least one sequence or one sequence fragment selected from the nucleotide sequences SEQ ID No. 22 or SEQ ID No. 24 or SEQ ID No. 26 for producing the polypeptides according to the invention.

The present invention also relates to a process for preparing the polypeptides according to the invention, according to which a cell containing a nucleotide sequence according to the invention is cultured under conditions for expressing said sequence and the polypeptide produced is recovered. In this case, the part encoding said polypeptide is generally placed under the control of signals which enable it to be expressed in a cell host. The choice of these signals (promoters, terminators, secretory leader sequence, etc.) can vary depending on the cell host employed. Furthermore, the nucleotide sequences of the invention can be part of a vector, which may be an autonomously replicating vector or an integrating vector. More specifically, autonomously replicating vectors can be prepared by using sequences for autonomous replication in the selected host. Integrating vectors can be prepared, for example, by using sequences which are homologous to particular regions of the host genome and which enable the vector to be integrated by homologous recombination.

The invention also relates to polyclonal or monoclonal antibodies or antibody fragments which are directed against a polypeptide as defined above. Such antibodies can be generated by methods which are known to the skilled person. In particular, these antibodies can be prepared by immunizing an animal against a polypeptide whose sequence is selected from the sequences SEQ ID No. 23 or SEQ ID No. 25 or SEQ ID No. 27 or any fragment or derivative of these sequences and then withdrawing blood and isolating the antibodies. These antibodies can also be generated by preparing hybridomas using the techniques known to the skilled person. The antibodies or antibody fragments according to the invention can, in particular, be used diagnostically for preparing Western blots (Maniatis, T. et al. 1989) which make it possible to identify the different JNK3 protein isoforms in accordance with their molecular weight by using a JNK3-specific antibody to visualise these proteins. These antibodies can also be the starting material for constructing ScFv, which, with the aid of suitable vectors (adenovirus, AAV, retrovirus, etc.), can be used in gene therapy for specifically inhibiting particular JNK3 isoforms in accordance with the technique described in WO94/29446 or in accordance with the technique described by Marasco (Marasco et al., 1997).

According to a preferred embodiment, the invention relates to antibodies which are specific for the JNK3α1 and JNK3α2 isoforms. These antibodies can, in particular, be monoclonal antibodies which are able to recognize an epitope which is located in the N-terminal part of the JNK3α1 and JNK3α2 forms. Advantageously, the epitope is an epitope which is contained in the fragment which is delimited by the amino acids which are located in positions 1 and 38 of the JNK3α1 and JNK3α2 forms; this fragment is depicted in the sequence SEQ ID No. 29. Such antibodies are able to induce a neuroprotective effect by specifically neutralizing the JNK3α1 and JNK3α2 forms. These antibodies are also able to impart specific properties to the protein which can modify its level of expression, its stability, its catalytic activity, its substrate specificity and its affinity for proteins which are involved in modulating these properties.

The invention also encompasses the antibodies which are derived from the above-defined monoclonal antibodies. Within the meaning of the present invention, derived antibodies are understood as being any molecule which comprises the idiotype of the monoclonal antibodies according to the invention, in particular chimeric antibodies, single-chain antibodies and Fab fragments. Such chimeric antibodies can be obtained using the techniques described by Morrison et al., J. Bacteriol. 159: 870 (1984); Neberger et al., Nature 312: 604–608 (1984); Takeda et al., Nature 314: 452–454 (1985), which publications are hereby incorporated into the present application by reference. The Fab fragments which contain the idiotype of the antibodies according to the invention can be generated by any technique known to the skilled person. The invention also relates to single-chain ScFv antibodies which are derived from the above-defined monoclonal antibodies. Such single-chain antibodies can be obtained using the techniques described in patents U.S. Pat. Nos. 4,946,778, 5,132,405 and 5,476,786.

The present invention also relates to a process for identifying compounds which are able to bind to the polypeptides according to the invention. The detection and/or isolation of these compounds can be effected in accordance with the following steps:

a molecule or a mixture containing various molecules, which may possibly not have been identified, is brought into contact with a polypeptide of the invention under conditions which would permit interaction between said polypeptide and said molecule if the latter were to possess an affinity for said polypeptide, and the molecules which are bound to said polypeptide of the invention are detected and/or isolated.

According to a particular embodiment, such a process makes it possible to identify molecules which are able specifically to block the JNK3ΔNα1 and JNK3ΔNα2 isoforms and thereby modulate the processes of neuronal degeneration. These molecules are capable of possessing a neuroprotective activity as a result of specifically inhibiting these isoforms. According to another embodiment, such a process makes it possible to identify specific inhibitors of the JNK3α1 and JNK3α2 isoforms.

The present invention also relates to processes for identifying compounds which are able to inhibit the activity of the derivatives of JNK3 according to the invention, by measuring the growth of microorganisms transformed with a nucleic acid encoding a polypeptide according to the invention. The detection and/or isolation of these compounds perhaps carried out using a negative screen for drug selection (the drug inhibits the growth of the yeast) or using a positive screen (the drug restores the growth of the yeast).

The latter avoids the selection of antifungal agents which distort the results.

These two screens use a Hog1 mutant expressing an isoform of JNK3. The first is used under hyperosmotic conditions. The second in addition contains the PBS2dd form which hyperstimulates the Hog1 pathway, inducing the death of the yeast under normal conditions. PBS2dd is only toxic if Hog1 is functional or replaced with JNK3.

The present invention therefore relates to a process for identifying compounds which inhibit the growth of microorganisms transformed with a nucleic acid encoding a polypeptide according to the invention, comprising the following steps:

a molecule or a mixture containing various molecules, which may possibly not have been identified, is brought into contact with at least one microorganism transformed with a nucleic acid encoding a polypeptide according to the invention, under conditions which permit the growth of said microorganism, and the molecules which inhibit the growth of said microorganism are detected and/or isolated.

It also relates to a a process for identifying compounds which permit the growth of microorganisms transformed with a nucleic acid encoding a polypeptide according to the invention, comprising the following steps:

a molecule or a mixture containing various molecules, which may possibly not have been identified, is brought into contact with at least one microorganism transformed with a nucleic acid encoding a polypeptide according to the invention, under conditions which inhibit the growth of said microorganism, and the molecules which permit the growth of said microorganism are detected and/or isolated.

This microorganism may be a yeast containing an inactive Hog1 gene and expressing one of the novel isoforms of JNK3 according to the invention, such as that described in the examples which follow, or any other microorganism having equivalent properties. This yeast grows under hyperosmotic conditions. Products which inhibit these novel isoforms of JNK3 are able to inhibit or slow down the growth of this strain under hyperosmotic conditions.

According to another embodiment, a mutated form of PBS2: PBS2$^{DD}$ (Wurgler-Murphy et al. 1997) which has a toxic effect on the growth of the yeast is expressed in the strain indicated above. This toxicity depends on the activity of the protein kinase located downstream which, according to the present invention, is a novel isoform of JNK3. Products which inhibit these novel isoforms of JNK3 are, in this case, able to inhibit the toxic effect of mutated PBS2 and thus to permit restoration of the growth of this strain.

The invention also relates to compounds or ligands which are able to inhibit the activity of the polypeptides according to the invention and which can be obtained using one of these microorganisms as a screening tool.

The invention also relates to compounds or ligands which are able to bind to the polypeptides according to the invention and which can be obtained using one of the above-defined processes.

The invention also relates to the use of a compound or ligand which has been identified and/or obtained using one of the above-described processes as a medicament. This is because such compounds can be used for preventing, ameliorating or treating various pathologies brought about by neuronal degeneration, among which may be mentioned Alzheimer's diseases, Huntington's disease and Parkinson's disease, senile dementias and dementias due to AIDS, cranial traumas, anoxias, hypoxias and cerebral oedemas.

The invention also relates to any pharmaceutical composition which comprises, as the active principle, at least one compound or ligand as defined above.

The polypeptides of the invention are also useful for identifying other partners involved in the mechanisms of neuronal degeneration or in the field of cardiac ischaemia by searching for and identifying molecules which interact in vivo with these polypeptides. In this respect, the present invention also relates to a process for identifying partner polypeptides which are specific for the different natural isoforms of JNK3. The specific partner polypeptides can be partner polypeptides which are specific for the JNK3α1ΔN or JNK3α2ΔN or hJNK3α139 forms or partner polypeptides which are specific for the JNK3α1 and JNK3α2 forms. The partner polypeptides which are specific for the different isoforms of JNK3 can be identified by the double hybrid cloning technique using the techniques described by Fields et al. 1994; the bait protein can, in particular, be the entire JNK3ΔNα1 or JNK3ΔNα2 protein or the N-terminal 38 amino acid extension of JNK3 which is lacking in the JNK3ΔN isoforms.

Other advantages of the present invention will be apparent from reading the examples which follow and which should be regarded as being illustrative and not limiting.

FIGURE LEGENDS

FIGS. 1a and 1b: comparison of the nucleotide sequences encoding the different human JNK3 isoforms. The nucleotide sequences of the 5' region of the DNA encoding different JNK3 isoforms have been aligned with respect to each other. In the first row are the 5' regions of DNA encoding hJNK3α1 and hJNK3α2, which are identical and superimposed (SEQ ID NO:32). In the second row, the 5' region of DNA encoding hJNK3α1 is superimposed upon the 5' region of DNA encoding hJNK3ΔNα2(SEQ ID NO:24). The 5' region of DNA encoding hJNK3α139 (SEQ ID NO:26) is in the third row. The difference in sequence as compared with the published sequences of JNK3α1 and 3α2 are indicated in bold and the termination codons supplied are underlined.

FIG. 2: comparison of the nucleotide sequences of the 5' region of DNA encoding human JNK3αΔN and rat SAPKβ. The nucleotide sequences of the 5' region of the human isoforms of JNK3Δα1 and ΔNα2 have been aligned with respect to that of rat SAPKβ. In the first row, the 5' regions of the DNA encoding human isoforms of JNK3Δα1 (SEQ ID NO:22) and JNK3ΔNα2 (SEQ ID NO;24 are superimposed upon each other. The 5' region of DNA encoding SAPKβ (SEQ NO:33) is set forth in the second row. The differences between the sequences are indicated by asterisks.

FIGS. 3a and 3b: comparison of the polypeptide sequences of the different human JNK3s. The polypeptide sequences of the different isoforms of JNK3 (hJNK3α1Δ (SEQ ID NO:23), hJNK3α2Δ (SEQ ID NO:25), hJNK3α139 (SEQ ID NO:27); hJNK3α1 (SEQ ID NO:30), and hJNK3α2 (SEQ ID NO:31) have been aligned with respect to each other, demonstrating a difference in the N-terminal region.

MATERIALS AND METHODS

1) Microorganisms Employed.

S. cerevisiae W303a : MATa, ade2, trp1, leu2, ura3, his3.
E. coli TG1: F' [traD 36, lacI$^q$, Δ (lacZ) M15, proA$^+$ B$^+$] supEΔ (hsdm-mcrb)5 ($r_K^-m_K^-$McrB$^-$), thi Δ (lac pro AB)

2) Culture Media

YPD medium (complete medium for yeasts): Bacto-yeast extract (Difco) 10 g/l, Bacto-peptone (Difco) 20 g/l, Glucose (Merk) 20 g/l. This medium can be solidified by adding agar (20 g/l) and sterilized by autoclaving at 110° C. for 20 min. If necessary, in order to achieve hyperosmotic conditions, 0.5M NaCl or 0.9M NaCl, or 1M Sorbitol, is added to this medium.

YNB Medium (minimal medium for yeasts): Bacto-yeast nitrogen base w/o amino acids (Difco) 6.7 g/l, Glucose (Merk) 20 g/l. This medium can be solidified by adding agar (20 g/l) and sterilized by autoclaving. The amino acids or the nitrogen bases which are required for the growth of the auxotrophic yeasts, and which have been previously sterilized by filtration, are then added at the rate of 50 mg/l. Ampicillin (100 μg/ml) can be added to this medium in order to prevent bacterial contamination.

LB (complete medium for bacteria): Bacto-yeast extract (Difco) 5 g/l, Bacto-tryptone (Difco) 10 g/l, NaCl (Difco) 5 g/l. This medium can be solidified by adding agar (12 g/l) and sterilized by autoclaving. Ampicillin is added to a concentration of 100 μg/ml in order to select the bacteria which have been transformed by the plasmids carrying the corresponding resistance marker.

3) Plasmids pIC20R: the plasmid pIC20R is a 2.7 kb bacterial plasmid derived from pUC19. It possesses a ColE1 origin of replication and a gene for resistance to ampicillin. This plasmid is used for cloning the protein kinase STE11. It possesses a multiple cloning site into which the sequences encoding the kinases are inserted.

pYX 232: the plasmid pYX 232 is a shuttle plasmid of 7.4 kb and 9.5 kb in size, respectively, which can be propagated and selected both in E. coli bacteria and in yeasts. It possesses a ColE1 origin of replication and a gene for resistance to ampicillin (propagation and selection in E. coli) as well as a 2 μm origin of replication and a TRP1 selection gene (selection in trp1 yeasts which are deficient for the synthesis of tryptophan). A multiple cloning site located downstream of the TPI (Triose Phosphate Isomerase) promoter permits insertion of the sequences of the genes to be expressed. Plasmid pYX232 is used for expressing the JNK1β1 and JNK2α1 proteins, and the different isoforms of human JNK3, in yeast. The sequences encoding these proteins were inserted into the EcoRI cloning site which had previously been rendered blunt-ended by digestion with the Klenow fragment of E. coli DNA polymerase.

pFA6a-kan MX4: the plasmid pFA6a-kan MX4 is a 2.5 kb plasmid which is derived from the plasmid pSP72 (Promega). The construction of plasmid pFA6a, and the introduction of a kanMX selection module derived from the E. coli transposon Tn903, have been described by Wach (Wach, 1994). This plasmid was used for deleting the gene encoding Hog1 in the strain W303a. The transformants are selected on medium to which geneticin (G418) has been added.

4) Synthesis Oligonucleotides

The sequences corresponding to the different JNKs were amplified with synthesis oligonucleotides and using double hybrid libraries of yeast genomic DNA or using plasmids.

Different synthesis oligonucleotides were generated for producing the deletion fragments, for performing the sequencing and for verifying deletion of the Hog1 gene in the yeast.

4.1—Oligonucleotides Employed for Amplifying Human JNK3 by PCR:

The oligonucleotides were chosen so as solely to amplify the open reading frame corresponding to JNK3α1 and 3α2. The initiation and termination codons are indicated in bold, and the restriction sites employed for cloning into the appropriate vectors are indicated in italics.

Oligonucleotide series employed for the human cerebellum cDNA library:

Oligonucleotide corresponding to the JNK3α1 and 3α2 5' region (SEQ ID No.1)
5'-GCG GGA TCC TAT GAG CCT CCA TTT CTT ATA CTA CTG CAG TGA ACC AAC-3'

Oligonucleotide corresponding to the JNK3α1 3' region (SEQ ID No.2)
5'-CAC GGT ACC TCA CTG CTG CAC CTG TGC TGA AGG AGA AGG C-3'

Oligonucleotide corresponding to the JNK3α2 3' region (SEQ ID No.3)
5'-GGC GGT ACC TCA CCT GCA ACA ACC CAG GGG TCC TGC CG-3'

Oligonucleotide series employed for the human cerebrum cDNA library:

Oligonucleotide corresponding to the JNK3α1 and 3α2 5' region (SEQ ID No.4)
5'-TCC CCC GGG ATC CAA AAT GAG CCT CCA TTT CTT ATA CTA C-3'

Oligonucleotide corresponding to the JNK3α1 3' region (SEQ ID No.5)
5'-TCC CCC GGG CTC GAG TCA CTG CTG CAC CTG TGC TGA-3' oligonucleotide corresponding to the JNK3α2 3' region (SEQ ID No.6)
5'-TCC CCC GGG CTC GAG TCA CCT GCA ACA ACC CAG GGG-3'

Oligonucleotide series employed for subcloning the ΔN isoforms of human JNK3:

Oligonucleotide corresponding to the JNK3ΔNα1 and ΔNα2 5' region (SEQ ID No. 7)
5'-TCC CCC GGG ATC CAA AAT GAG CAA AAG CAA AGT TGA CAA-3'

Oligonucleotide corresponding to the JNK3ΔNα1 3' region (SEQ ID No.8)
5'-TCC CCC GGG CTC GAG TCA CTG CTG CAC CTG TGC TGA-3'

Oligonucleotide corresponding to the JNK3ΔNα2 3' region (SEQ ID No.9)
5'-TCC CCC GGG CTC GAG TCA CCT GCA ACA ACC CAG GGG-3'

4.2—Oligonucleotides Employed for Amplifying Human JNK1β1 and JNK2α1 by PCR:

The oligonucleotides were selected so as solely to amplify the open reading frame corresponding to JNK1β1 and JNK2α1. The initiation and termination codons are indicated in bold and the restriction sites employed for cloning into the yeast expression vector are indicated in italics.

Oligonucleotides for amplifying JNK1β1

Oligonucleotide corresponding to the JNK1β1 5' region (SEQ ID No.10)
5'-TCC CCC GGG ATC CAA AAT GAG CAG AAG CAA GCG TGA C-3'

Oligonucleotide corresponding to the JNK1β1 3' region (SEQ ID No.11)

5'-TCC CCC GGG CTC GAG TCA CTG CTG CAC CTG TGC-3'

Oligonucleotides for amplifying JNK2α1:

Oligonucleotide corresponding to the JNK2α1 5' region (SEQ ID No.12)
5'-TCC CCC GGG ATC CAA AAT GAG CGA CAG TAA ATG TGA C-3'

Oligonucleotide corresponding to the JNK2α1 3' region (SEQ ID No. 13)
5'-TCC CCC GGG CTC GAG TTA CTG CTG CAT CTG TGC TGA-3'

4.3—Oligonucleotides Employed for Performing and Validating Deletion of the Hog1 Gene in Yeast:

Oligonucleotides employed for deleting the Hog1 gene in yeast:

The first pair of oligonucleotides hybridizes with the gene for resistance to G418 and with the yeast Hog1 gene upstream of the initiation codon (SEQ ID No. 14) or downstream of the termination codon (SEQ ID No. 15):
5'-TAGGACACAGATATTCGGTACAGCTGAAGCTT CGTACGC-3' (SEQ ID No. 14)
5'-GACCTTTGTTTCCACCAGCTGCATAGGCCACT AGTGGATCTG-3' (SEQ ID No. 15)

The second pair of oligonucleotides hybridizes with the yeast Hog1 gene and with the part of the first pair of oligonucleotides corresponding to the sequence of the Hog1 gene (SEQ ID No. 14 or 15):
5'-ACCACTAACGAGGAATTCATTAGGACACAGAT ATTCGGTA-3' (SEQ ID No. 16)
5'-TTTGCAGCTACATGATCGCTGACCTTTGTTTC CACCAGCT-3' (SEQ ID No. 17)

Oligonucleotides for validating deletion of the Hog1 gene in yeast:

Oligonucleotides for amplifying a part of the undeleted Hog1 gene:
5'-GAG TAG TAA TTA CTT TCT TG-3' (SEQ ID No. 18)
5'-CCG TGA CAA AAT ATA TAT CTT CC-3' (SEQ ID No. 19)

Oligonucleotides for amplifying a part of the Hog1 gene which has been deleted by inserting the gene for resistance to G418:
5'-GAG TAG TAA TTA CTT TCT TG-3' (SEQ ID No.20)
5'-GGA TCT TGC CAT CCT ATG G-3' (SEQ ID No.21)

5) Preparing Plasmid DNA:

The small-scale or large-scale plasmid DNA preparations were carried out using the protocols described by Maniatis et al. (1989).

6) Chain Amplification Using Thermostable Taq Polymerase (or PCR):

PCR enables a DNA sequence to be amplified between two known regions to which oligonucleotides (of approximately 20 nucleotides), which will serve as primers for a thermostable polymerase, are able to bind. The reactions are carried out in a final volume of 100 ml in the presence of the DNA template (50 ng), dNTP (0.2 mM), PCR buffer (10 mM TrisHCl pH 8.5; 1.5 mM $MgCl_2$; 5 mM KCl; 0.01% gelatin), two oligonucleotides (500 ng each) and 2.5 IU of Ampli Taq DNA polymerase. The mixture is covered with 2 drops of paraffin oil in order to restrict evaporation of the sample. The programme employed comprises 32 cycles: 1 cycle of template denaturation (5 min at 95° C.), 30 cycles (1 min of denaturation at 94° C., 1 min of hybridization of the oligonucleotides with the DNA template at 50° C., 1 min of elongation using the Taq polymerase at 72° C.), and lastly 1 cycle of final elongation (5 min at 72° C.). The PCR can be carried out directly on cultures of bacteria or yeasts which are in the exponential phase of growth instead of on the DNA template.

7) Fluorescence Sequencing:

The sequencing technique employed is derived from the method of Sanger et al. (1977) and adapted for the fluorescence sequencing developed by Applied Biosystems. The protocol employed is that described by the system conceivers (Perkin Elmer, 1995).

8) Insertion of a DNA Fragment into a Plasmid by Ligation:

The insert originating from a plasmid DNA or a PCR reaction is digested for 1 h with appropriate restriction enzymes which are used at the rate of 1 U/mg of DNA and in their respective buffers (Biolabs). The fragments derived from the digestion are separated in accordance with their size by electrophoresis on a "preparative" 0.8% agarose gel which has been prepared in a TBE buffer (90 mM Tris, 90 mM Borate, 20 mM EDTA PH8) containing 0.5 μg of ethidium bromide/ml. Loading Blue (1/10th volume) is added to the samples before they are loaded onto the gel alongside a molecular weight marker (1 KB Ladder, Gibco BRL). The gel is run at a constant 90 volts/$cm^2$ in the TBE buffer. The DNA is visualized under UV by the fluorescence of the ethidium bromide, which is intercalated between the bases. The pieces of gel containing the DNA fragments of desired size (vectors and inserts) are excised with a scalpel, introduced into a dialysis bag containing TBE and subjected to electrophoresis at 90 volts for 30 min. The DNA which has been extracted from the gel is then recovered, treated with one volume of phenol/chloroform/isoamylate (25/24/1), precipitated with 3 volumes of absolute ethanol in the presence of 0.25M NaCl, washed once with 70% ethanol, dried and finally redissolved in 20 μl of $H_2O$. After having estimated the respective quantities of vector and insert on a gel, they are mixed in a ratio of 1/1 in the presence of 40 IU of T4 DNA ligase, 1×final concentration of ligation buffer (50 mM TrisHCl PH 7.5, 10 mM $MgCl_2$, 1 mM ATP) in a total volume of 20 μl. The ligation is carried out at 20° C. for at least 1 h.

9) Transformation of the Bacteria with a Plasmid:

The so-called "TSB" method (Chung et al., 1988): this method consists in weakening the wall of the bacteria by treating with DMSO in order to permit entry of the DNA into the cells. Its efficacy is $10^6$ transformants/μg of DNA. The bacteria are cultured in liquid LB medium for approximately 3 h with shaking (up to $A_{600}$=0.6). The culture is centrifuged at 3000 rpm for 10 min and the pellet is taken up in 1/10th of the initial volume by TSB (LB medium, 10% $PEG_{4000}$, 5% DMSO, 10 MM $MgCl_2$, 10 mM $MgSO_4$) and incubated at 4° C. for 15 min. Approximately 50 ng of DNA (10 μl in the case of the ligation product) are added to 100 μl of competent bacteria and the mixture is then incubated at 4° C. for 30 min. After adding TSBglu (TSB, 20 mM glucose) and incubating at 37° C. for 1 h, the bacteria are spread out on LB agar medium containing ampicillin.

10) Transformation of Yeast With an Expression Vector:

The yeast cells are rendered competent by treating them with LiAc/PEG in accordance with the method described by Gietz (Gietz et al., 1995).

The yeast cells are cultured on YPD solid medium at 28° C. overnight. They are then resuspended in 1 ml of sterile solution I (0.1M LiAc, 10 mM Tris HCl, 1 mM EDTA pH 7.5), centrifuged at 3000 rpm for 1 min and once again taken up in 1 ml of solution I. 50 μl of the suspension are then mixed with 5 μg of salmon sperm DNA (carrier DNA), from 1 to 5 μg of plasmid DNA and 300 μl of sterile solution II (0.1M LiAc, 10 mM Tris HCl, 1 mM EDTA PH 7.5, 50% $PEG_{4000}$). The mixture is incubated at 28° C. for 30 min and then subjected to a thermal shock at 42° C. for 20 min. After having been centrifuged at 3000 rpm for 1 min, the cells are washed once with sterile water and taken up in 100 µl of sterile water. The yeast cells are then spread out on YNB agar medium to which amino acids required for their growth have been added. In order to enable the transformed yeast strains to be selected, the amino acids and nitrogen bases corresponding to the selection markers carried by the plasmids are not added. After the yeast cells have been spread out, the plates are incubated at 28° C. for 3 days.

11) Drop Test:

This test enables the phenotype of a yeast strain to be analysed. One drop (approximately 5 µl) of a slightly turbid suspension of yeast cells (approximately $10^5$ cells/ml) is deposited on various hyperosmotic and non-hyperosmotic agar media and growth is observed following 2 days of incubation at 28° C.

EXAMPLES

Example 1

Cloning cDNA Encoding Novel Human JNK3 Isoforms: JNK3ΔNα1, JNK3ΔNα2 and JNK3α139

The molecular cloning of human JNK3 was carried out by PCR using an expression library of human cerebellum cDNA (Clontech®) or a double hybrid library of human cerebrum cDNA (Clontech®). The nucleotide primers were selected so as to amplify, by PCR, the open reading frame corresponding to JNK3α1 and 3α2 (Genbank U34820 and U34819) (see Materials and Methods).

A first series of oligonucleotides employed for amplifying JNK3 from the cerebellum library supplied BamHI and KpnI cloning sites in the 5' and 3' positions, respectively, for being able to introduce the amplified DNA fragments into appropriate cloning or expression vectors (SEQ ID No. 1, SEQ ID No. 2 and SEQ ID No. 3).

The second series, which was employed on the cerebrum cDNA two hybrid library, introduced SmaI and BamHI sites in the 5' position and SmaI and XhoI sites in the 3' position (SEQ ID No. 4, SEQ ID No. 5 and SEQ ID No. 6).

The PCR reaction was carried out using 1 µg of DNA from one of the two expression libraries and 0.5 µg of each oligonucleotides flanking the region to be amplified. The resulting DNA fragments were cloned into cloning vectors which were suitable for analysing their sequence.

It was noted that, among the entirety of the fragments isolated, the sequences corresponding to the already-described JNK3α1 and 3α2 were in a minority as compared with those corresponding to three novel isoforms.

A comparison of the sequences of these isoforms is presented in FIG. 1. It can be seen that two sequences, termed JNK3Δnα1 and JNK3ΔNα2, are comparable with JNK3α1 and 3α2, respectively, and exhibit an insertion of 27 nucleotides in position +66 with respect to the ATG. This sequence, which is very homologous with the 5' non-coding sequence of rat SAPKβ (FIG. 2), supplies a termination codon which implies initiation at the second ATG.

The complete nucleotide sequence of JNK3ΔNα1 is depicted in sequence SEQ ID No. 22, and the complete nucleotide sequence of JNK3ΔNα2 is depicted in sequence SEQ ID No. 24. The corresponding polypeptide sequences are depicted in sequences SEQ ID No. 23 (JNK3ΔNα1) and No. 25 (JNK3ΔNα2), respectively.

The protein which is expressed from these sequences exhibits a deletion of 38 amino acids corresponding to the N-terminal extension of JNK3, which distinguishes it from the other JNKs (FIG. 3).

The third sequence, corresponding to the JNK3α139 isoform, is characterized by replacement of the nucleotide C with T in position 418 from the ATG in the part possessed in common by JBK3α1 and JNK3α2 (FIG. 1). This mutation creates a termination codon. A large part of the C-terminal region of JNK3 is deleted from the protein which is expressed from this sequence. This polypeptide only comprises the first 139 amino acids possessed in common by JNK3α1 and 3α2 (FIG. 3), which includes the ATP-binding site. The nucleotide sequence of JNK3α139 is depicted in SEQ ID No. 26, and the corresponding polypeptide sequence is depicted in sequence SEQ ID No. 27.

Example 2

Constructing a Yeast Strain Which is Mutated in the Hog1 Gene

Studies showed that it was possible to complement a yeast which was mutated in the Hog1 gene, which is homologous to mammalian JNKs, with the human JNK1 gene (Galcheva-Garvona et al. 1994) or with the mouse p38 gene (Han et al. 1994). In yeast, the Hog1 gene is involved in a pathway of response to hyperosmotic stresses which ends in a synthesis of intracellular glycerol for the purpose of offsetting the differences in osmotic pressure as compared with the external medium. A yeast model was therefore selected for evaluating the functional properties of N-terminally truncated JNK3 isoforms (JNK3ΔNα1, JNK3ΔNα2) and comparing them with those of the other known isoforms of JNK3.

In order to generate this model, it is necessary to interrupt the hyperosmotic stress response pathway in the yeast by introducing a mutation within the Hog1 gene. Such a mutant should be unable to grow on a medium containing high concentrations of salt such as NaCl (0.5M or 0.9M) or of sorbitol (1M). It is used for testing, by means of complementation, whether the different isoforms of human JNK3 are able to restore cell growth under conditions of hyperosmotic stress.

Deleting the Hog1 Gene of *S. cerevisiae* With a Disruption Cassette Containing the Marker for Resistance to G418.

Deleting the Hog1 gene was effected using the technique described by Wach (Wach et al. 1994). This technique employs a DNA deletion fragment which is obtained directly by PCR. This fragment corresponds to a part of the sequence of the gene to be destroyed, with the gene being interrupted by a resistance marker. In order to construct this fragment, use was made of a pair of oligonucleotides whose sequence enables the gene for resistance to G418 to be amplified, by means of PCR, while at the same time generating sequences corresponding to the gene to be destroyed at the ends of the amplified fragment. This resistance marker is under the control of the promoter and terminator of a strongly expressed gene, i.e. the *Ashbya gossypii* TEF gene.

Two pairs of oligonucleotides were synthesized for producing the fragment for deleting the Hog1 gene. The first pair (SEQ ID No. 14 and SEQ ID No. 15) hybridizes to the terminal ends of the gene for resistance to G418 which is carried by the plasmid pFA6a-kanMX4. These oligonucleotides also each contain a short floating sequence of 20 base pairs, with each floating sequence corresponding, respectively, to the region just upstream of the ATG and downstream of the Hog1 stop codon. The second pair of oligonucleotides (SEQ ID No. 16 and SEQ ID No. 17) enables these floating sequences to be extended by 20 base pairs in a second PCR step. The aim of this extension is to increase the frequency of crossing over in these floating sequences and therefore the frequency of deleting the Hog1 gene.

The deletion fragment was prepared in two PCR steps using the plasmid pFA6a-kan MX4 as the template in the first step and the product of the first PCR in the second step. The fragment was used to transform the strain W303a.

The transformed strains were first of all selected for their resistance to G418, which is conferred by the deletion fragment, and then for the osmosensitivity phenotype corresponding to the total inactivation of the hyperosmotic stress pathway as a result of deleting the Hog1 gene. Out of four G418 strains selected, two strains exhibited the osmosensitivity phenotype which corresponds to the inability of the strains to grow on complete medium (YPD) containing 0.5M or 0.9M sodium chloride (NaCl) or 1M sorbitol.

In order to verify that the Hog1 gene was indeed deleted in these strains, a PCR amplification was carried out on their genomic DNA. Use was made of two pairs of oligonucleotides which enabled the deleted Hog1 gene or the undeleted Hog1 gene, respectively, to be amplified (see Materials and Methods).

The pair of oligonucleotides (SEQ ID No. 20 and SEQ ID No. 21) employed for amplifying the region corresponding to the deleted Hog1 gene only enabled a PCR fragment to be obtained on the genomic DNA derived from the osmosensitive strains, thereby demonstrating that these strains were indeed deleted in the Hog1 gene. Conversely, the other pair of oligonucleotides (SEQ ID No. 18 and SEQ ID No. 19) were only able to generate a fragment from the genomic DNA of the osmoresistant strains. This confirms that these strains are not deleted in the Hog1 gene. The yeast strain which is deleted in the Hog1 gene is designated yIM1.

Example 3

Complementing the Osmosensitive Yeast Strain With the Different Human JNK3 Isoforms This example illustrates the properties of the different human JNK3 isoforms. The test of complementing the osmosensitive strain mutated in the Hog1 gene (yIM1) was performed with the different JNK3 isoforms. The JNK1β1 (u35004) and JNK2α1 (u34821) kinases were used as controls. Since the kinases have a function which is homologous to that of the HOG1 kinase in this test, they are able to restore the growth of the yIM1 yeast under hyperosmotic stress conditions.

Constructing Expression Vectors for Expressing the Different JNKs in Yeast.

The expression vector pYX232 (R&D), which replicates in high copy number in the cell, was chosen for expressing the different JNKs in yeast. It possesses the Trp1 gene as the selection marker and an expression cassette which consists of the TPI (Triose phosphate isomerase) promoter and a polyA sequence separated by a multicloning site. The different inserts, encoding JNK1β1, JNK2α1 and the human JNK3 isoforms, were introduced into the EcoRI site of this plasmid, which site had previously been cleaved with the corresponding restriction enzyme and rendered blunt-ended using the Klenow fragment of DNA polymerase I.

The JNK1β1, JNK2α1, JNK3α1, JNK3α2, JNK3ΔNα1 and JNK3ΔNα2 fragments were obtained by PCR from plasmids containing the corresponding cDNA and using the oligonucleotides described in Materials and Methods (SEQ ID No. 10 and No. 11 for amplifying the fragment encoding JNK1β1, SEQ ID No. 12 and No. 13 for amplifying the fragment encoding JNK2α1, SEQ ID No. 4 and No. 5 for amplifying the fragment encoding JNK3α1, SEQ ID No. 4 and No. 6 for amplifying the fragment encoding JNK3α2, SEQ ID No. 7 and No. 8 for amplifying the fragment encoding JNK3ΔNα1, and SEQ ID No. 7 and No. 9 for amplifying the fragment encoding JNK3ΔNα2), each of which oligonucleotide pairs introduced a SmaI restriction site at each end.

These fragments were cleaved with the enzyme SmaI to enable them to be introduced, by ligation, into plasmid pYX232. All these constructs were checked by sequencing in order to verify that the inserts had been introduced into the corresponding restriction sites and that they did not contain any mutations generated by the PCR reaction.

Test for Complementing the Hog1—Osmosensitive Strain With the Different JNK-expressing Vectors.

The different constructs permitting expression of the human JNKs, and plasmid pYX332 without insert, were used to transform the Hog1-osmosensitive yeast. The clones containing the different plasmids were selected on YNB minimal medium to which had been added amino acids or nitrogen bases which were required for growing the W303a strain, apart from tryptophan. Three clones corresponding to each construct were analysed by drop test on complete medium containing 0.5 or 0.9M NaCl or 1M sorbitol. The strains are incubated at 30 degrees for three days. The results are presented in the table below.

|  | YPD without NaCl | YPD + 1M sorbitol | YPD + 0.5 M NaCl | YPD + 0.9 M NaCl |
|---|---|---|---|---|
| W303 wild-type strain | +++ | +++ | +++ | +++ |
| yIM1 (W303 deleted for Hog1) | +++ | – | – | – |
| yIM1 + JNK1β1 | +++ | +++ | +++ | ++ |
| yIM1 + JNK2α1 | +++ | ++ | ++ | – |
| yIM1 + JNK3α1 | +++ | – | – | – |
| yIM1 + JNK3α2 | +++ | – | – | – |
| yIM1 + JNK3ΔNα1 | +++ | ++ | ++ | – |
| yIM1 + JNK3ΔNα2 | +++ | ++ | ++ | – |

The different strains shown in the 1st column are tested in culture on different complete media (YPD) to which Sorbitol or NaCl have or have not been added, as indicated in columns No. 2 to No. 5. The + sign indicates ability to grow while the – sign indicates absence of growth.

The clones transformed with the plasmids encoding JNK1β1, JNK2α1 and two of the JNK3 isoforms in which the N-terminal region is deleted (JNK3ΔNα1 and JNK3ΔNα2) are able to grow on complete medium containing 0.5M NaCl or 1M sorbitol. The clones expressing JNK1β1 are the only ones which exhibit slight growth on medium containing 0.9M NaCl.

By contract, the strains transformed with the plasmid without insert or the plasmids encoding JNK3α1 and JNK3α2 only grow under non-hyperosmotic medium conditions. JNK1β1, JNK2α1 and two of the JNK3 isoforms whose N-terminal region has been deleted (JNK3ΔNα1 and JNK3ΔNα2) are therefore functional in yeast and able to replace the HOG1 kinase.

These results indicate that the absence of the fragment corresponding to the first 38 amino acids of the known isoforms of JNK3 (JNK3α and JNK3α2) imparts on the JNK3ΔNα1 or JNK3ΔNα2 isoforms a function which is homologous to that of the HOG1 kinase. This function is found in the JNK1β1 and JNK2α1 isoforms, which also lack the fragment corresponding to the first 38 amino acids of JNK3α and JNK3α2. Conversely, the presence of the fragment corresponding to the first 38 amino acids of the known isoforms of JNK3 (JNK3α and JNK3α2) is associated with the absence, in these isoforms, of the function which is homologous to that of the HOG1 kinase.

These novel isoforms therefore exhibit an activity in yeast which is different from that of the two forms of JNK3 which are described in the literature. This difference may be associated with the process of activating these kinases in yeast. As in the case of JNK1 or p38, it was shown that the novel isoforms of JNK3 are activated by the MapKinase Kinase PBS2 in yeast since a hog1, pbs2 double mutant yeast strain to which the novel isoforms of JNK3 have been added is unable to grow under hyperosmotic conditions. Similarly, it is possible that these novel isoforms possess a substrate specificity which is different from that of the previously described JNK3s and which enables them to activate the hyperosmotic stress response pathway in yeast.

References

Anderson, A. J. et al. (1994). Increased immunoreactivity for Jun- and Fos-related proteins in Alzheimer's disease: association with pathology. *Exp. Neurol.* 125, 286–295.

Chung, C T. et al. (1989). One-step preparation of competent *Escherichia coli:* transformation and storage of bacterial cells in the same solution. *Proc. Natl. Acad. Sci. USA.* 86, 2172–2175.

Derijard, B. et al. (1994). JNK1: a protein kinase stimulated by UV light and HaRas that binds and phosphorylates the c-Jun activation domain. *Cell,* 76, 1025–1037.

Estus, S. et al. (1994). Altered gene expression in neurones during programmed cell death: identification of c-jun as necessary for neuronal apoptosis. *J. Cell. Biol.* 127, 1717–1727.

Field, S. et al. (1994). The two-hybrid system: an assay for protein-protein interactions. T.I.G. 10, 286–292.

Galcheva-Gargova, Z. et al. (1994). An osmosensing signal transduction pathway in mammalian cells. *Science.* 265, 806–808.

Gietz, R D. et al. (1995). Studies on the transformation of intact yeast cells by the LiAc/SS-DNA/PEG procedure. *Yeast.* 11, 355–360.

Gupta, S. et al (1996). Selective interaction of JNK protein kinase isoforms with transcription factors. *EMBO j.* 15, 2760–2770.

Han, J. et al. (1994). A MAP kinase targeting by endotoxin and hyperosmolarity in mammalian cells. *Science.* 265, 808–811.

Ham, J. et al. (1995). A c-Jun dominant negatif mutant protects sympathetic neurones against programmed cell death. *Neurone.* 14, 927–939.

Herdegen, T. et al. (1997). The c-Jun protein-transcriptional mediator of neuronal survival, regeneration and death. *Trends Neurosci.* 20, 227–231.

Herdegen, T. et al. (1998). Lasting N-terminal phosphorylation of c-Jun and activation of c-Jun N-terminal kinases after neuronal injury. *J. Neurosci.* 18, 5124–5135.

Maniatis, T. et al. (1989). Molecular cloning, second edition. Cold Spring Harbor Laboratory. Cold Spring Harbor, N.Y.

Marasco, W. A. (1997). Intrabodies: turning the humoral immune system outside in for intracellular immunisation. Gene therapy. 4, 11–15.

Martin, G. et al. (1996). Jun expression is found in neurones located in the vicinity of subacute plaques in patients with multiple sclerosis. *Neurosci. Lett.* 212, 95–98.

Mohit, A A. et al. (1996). p493F12 kinase: a novel MAP kinase expressed in a subset of neurons in the human nervous system. Brain Res Mol Brain Res. 35, 47–57.

Sanger, F. et al. (1977). DNA sequencing with chain terminating inhibitors. *Proc. Natl. Acad. Sci. USA.* 74, 5463–5467.

Wach, A. et al. (1994). New heterologous modules for classical or PCR-based gene disruptions in *Saccharomyces cerevisiae.* Yeast. 10, 1793–1808.

Wurgler-Murphy, S. et al. (1997). Regulation of the Saccharomyces cerevisiae HOG1 mitogen-activated protein kinase by the PTP2 and PTP3 protein tyrosine phosphatases. *Mol. Cell. Biol.* 17, 1289–1297.

Yang, D D. et al. (1997). Absence of excitotoxicity-induced apoptosis in the hippocampus of mice lacking the Jnk3 gene. *Nature.* 389, 865–869.

Zhang, Y. et al. (1998). A splicing variant of a death domain protein that is regulated by a mitogen-activated kinase is a substrate for c-Jun N-terminal kinase in the human central nervous system. *Proc. Natl. Acad. Sci. USA.* 95, 2586–2591.

What is claimed is:

1. An isolated nucleic acid comprising the nucleotide sequence of SEQ ID NO:24.

2. An expression vector comprising the isolated nucleic acid of claim 1 operatively associated with a promoter.

3. A host cell transformed or transfected with the expression vector of claim 2.

4. A method for making a polypeptide, comprising the steps of:
   (a) growing a culture of the host cell of claim 3 in a suitable culture medium; and
   (b) purifying the polypeptide from the culture medium.

* * * * *